United States Patent
Addison et al.

(10) Patent No.: US 10,314,748 B2
(45) Date of Patent: Jun. 11, 2019

(54) SILICONE GEL-COATED WOUND DRESSING

(71) Applicant: KCI USA, INC., San Antonio, TX (US)

(72) Inventors: Deborah Addison, Via Lancaster (GB); Sally Stephens, Skipton (GB); Rachel Hadley, Earby (GB)

(73) Assignee: KCI USA, INC., San Antonio, TX (US)

(*) Notice: Subject to any disclaimer, the term of this patent is extended or adjusted under 35 U.S.C. 154(b) by 600 days.

(21) Appl. No.: 15/051,466

(22) Filed: Feb. 23, 2016

(65) Prior Publication Data
US 2016/0250077 A1    Sep. 1, 2016

Related U.S. Application Data

(62) Division of application No. 13/820,414, filed as application No. PCT/GB2011/001258 on Aug. 22, 2011, now Pat. No. 9,295,749.

(30) Foreign Application Priority Data

Sep. 3, 2010    (GB) .................................. 1014705.6

(51) Int. Cl.
  *A61F 13/02*    (2006.01)
  *B65B 55/02*    (2006.01)
  (Continued)

(52) U.S. Cl.
  CPC .... *A61F 13/0266* (2013.01); *A61F 13/00076* (2013.01); *A61F 13/0253* (2013.01);
  (Continued)

(58) Field of Classification Search
  CPC ............ A61F 13/0266; A61F 13/00076; A61F 13/0253; A61F 13/0283; A61F 13/00991;
  (Continued)

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael I Morykwas, PHD; Vacuum-Assisted Closure: A New Method for Wound Control and Treatment: Clinical Experience; Annals of Plastic Surgery.
(Continued)

*Primary Examiner* — Ophelia A Hawthorne
(74) *Attorney, Agent, or Firm* — Foley & Lardner LLP (57) ABSTRACT

A wound dressing product that includes a substrate layer having an upper surface and a lower surface; a tacky silicone coating composition present on the upper surface and on the lower surface; and upper and lower release sheets covering the substrate and the tacky silicone coating composition on the upper and lower surfaces, respectively, and adhered to the surfaces by the tacky silicone coating composition, wherein the upper surface is less tacky than the lower surface whereby the upper release sheet can be removed from the upper surface more readily than the lower release sheet can be removed from the lower surface. Also provided are methods for making such dressings.

17 Claims, 4 Drawing Sheets

(51) Int. Cl.
*A61L 15/26* (2006.01)
*A61F 13/00* (2006.01)
*A61L 15/24* (2006.01)
*A61L 15/58* (2006.01)

(52) U.S. Cl.
CPC .......... *A61F 13/0283* (2013.01); *A61L 15/24* (2013.01); *A61L 15/26* (2013.01); *A61L 15/58* (2013.01); *B65B 55/02* (2013.01); *A61F 13/00991* (2013.01); *A61F 2013/00289* (2013.01); *A61F 2013/00617* (2013.01); *A61F 2013/00702* (2013.01); *A61F 2013/00897* (2013.01); *A61L 2420/00* (2013.01)

(58) Field of Classification Search
CPC .. A61F 2013/00289; A61F 2013/00617; A61F 2013/00702; A61F 2013/00897; A61L 15/24; A61L 15/26; A61L 15/58; A61L 2420/00; B65B 55/02
See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Mute |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carlon |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,846,508 B1 * | 1/2005 | Colas ............... A61L 15/58 427/2.1 |
| 9,295,749 B2 | 3/2016 | Addison et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2016/0250088 A1 | 9/2016 | Williamson et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2611468 A1 | 7/2013 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 2006-181816 A | 7/2006 |
| JP | 4129536 B2 | 8/2008 |
| SG | 71559 | 4/2002 |
| WO | 80/02182 A1 | 10/1980 |

(56) References Cited

FOREIGN PATENT DOCUMENTS

| WO | 87/04626 A1 | 8/1987 |
|----|-------------|--------|
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2012028842 A1 | 3/2012 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
M.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Office Action in BR Application No. 112013005100-0, dated Jul. 9, 2018 (English translation).
Office Action in CA Application No. 2809753, dated Jun. 6, 2018 (4 pages).
Requisition by Examiner corresponding to Canadian Application No. 2,809,753 dated Sep. 28, 2017.

* cited by examiner

SILICONE GEL-COATED WOUND DRESSING

The present application is a divisional of U.S. Non-Provisional patent application Ser. No. 13/820,414, filed Mar. 1, 2013, which claims the benefit of PCT/GB2011/001258, filed Aug. 22, 2011, which claims the benefit of GB 1014705.6, filed Sep. 3, 2010, all of which are incorporated herein by reference for all purposes.

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable.

STATEMENT REGARDING PRIOR DISCLOSURES BY THE INVENTOR OR A JOINT INVENTOR

Not Applicable.

FIELD OF THE INVENTION

The present invention relates to wound dressings comprising a substrate coated on both surfaces with a tacky silicone gel, wherein the surfaces have different tackiness, and to methods of making such dressings.

BACKGROUND OF THE INVENTION

Dressing materials for application to the surface of wounds should desirably be nonadherent to the moist wound surface, but sufficiently tacky to allow attachment of the dressing to intact skin around the wound and attachment to further dressing layers such as absorbent layers. For this purpose a soft or tacky hydrophobic material is suitable for the material. The wound contacting material should desirably be liquid-permeable to allow passage of wound fluid, especially for heavily exuding wounds such as burns. The material should also be non-irritating, inexpensive, and stable to common sterilization methods such as ionizing radiation.

Traditional tulle gras dressings generally consist of a layer of gauze coated with paraffin wax. Such dressings have a number of desirable properties, and for this reason have been used extensively for many years. Among these advantages are their high degree of conformability and deformability, and the fact that their tackiness makes them very easy to apply. That is to say, a tulle gras dressing applied to a wound will usually remain in place simply by adhesion of the paraffin wax to the patient's skin (or to itself in the case of a dressing wrapped around a finger, for example) while a securing bandage is applied. Tulle gras dressings are also quite inexpensive. However, tulle gras dressings do have a number of disadvantages. Principal amongst these is that, although initially nonadherent, they often become "dry" (in the sense of losing their paraffin coating) and consequently adhere to the wound to which they are applied. This effect is due to the paraffin coating becoming mobile at body temperatures and migrating into the wound or being absorbed into the backing of the dressing or bandage. In some cases, removal of a tulle gras dressing which has become dry in this way can cause considerable trauma. Indeed, it is quite common to have to soak tulle gras dressings in order to remove them. If tulle gras dressings are changed more frequently, in an attempt to avoid them becoming attached to the wound, this may delay wound healing and adds to nursing costs.

A further disadvantage of traditional tulle gras dressings is that fibres from the gauze may become incorporated in the wound, as may the paraffin coating of the dressing. Some authorities see the migration of paraffin into a wound as an undesirable effect and any paraffin found in a wound can be difficult to remove with normal aqueous wound cleansing agents. Moreover, the pores of the gauze may become occluded if the paraffin coating is too heavy or as a result of the mobility of the paraffin during use of the dressing. While occlusive dressings are appropriate in some circumstances, it is undesirable that the nursing staff should have no control over whether the dressing used is in fact occlusive.

Still further disadvantages of conventional tulle gras dressings are that they are effectively opaque and of somewhat unsightly appearance, and the paraffin can run during storage, making them particularly messy to apply.

EP-A-0251810 describes wound dressing materials that overcome the above disadvantages by replacing the paraffin wax coating of conventional tulle gras by a tacky or non-tacky, hydrophobic silicone coating on a gauze or mesh substrate. In certain embodiments, the gauze may be provided with a tacky silicone coating on one side and a non-tacky silicone coating having a different composition on the other side. Similar materials are described in WO-A-8705206.

EP-A-0342950 describes similar wound dressings having a non-adherent silicone coating. The adherence of the silicone is reduced by addition of an amine-extended polyurethane.

BRIEF SUMMARY OF THE INVENTION

Not Applicable.

DETAILED DESCRIPTION OF THE INVENTION

The present invention provides a wound dressing product comprising: a substrate layer having an upper surface and a lower surface; a tacky silicone coating composition present on said upper surface and on said lower surface; and upper and lower release sheets covering said substrate and said tacky silicone coating composition on said upper and lower surfaces, respectively, and adhered to said surfaces by said tacky silicone coating composition, wherein said upper surface is less tacky than said lower surface whereby said upper release sheet can be removed from said upper surface more readily than said lower release sheet can be removed from said lower surface.

Suitably, the substrate is porous, whereby the substrate is permeable to the fluid. For example, the substrate may be a mesh or web or fabric suitably formed from a woven, nonwoven or knitted textile or a molded mesh.

In certain embodiments the substrate is a fabric such as a gauze, or a mesh, having an array of apertures. The size and shape of the apertures in the substrate are not critical, but the apertures should suitably be such as to ensure that the material can be adequately coated with silicone gel without them becoming occluded. The apertures generally have an aspect ratio of from 1:1 to 5:1, and preferably from 1:1 to 2:1. For example, the apertures may be approximately circular or approximately square. The apertures suitably have an average diameter of from 0.3 to 4 mm, and more suitably from 0.5 to 2 mm.

The substrate is suitably formed from any medically acceptable material, such as cellulose, polyolefins, polyesters, or polyamides. An especially suitable material is cellulose acetate gauze. Substrates having a weight of from 15 to 200 g/m$^2$ are generally found to be suitable for use in the products of the invention, and fabrics weighing from 50 to 150 g/m$^2$ are most suitable. For example, certain embodiments employ a fabric of from 80 to 120 g/m$^2$.

Suitably, the silicone-coated substrate product retains open apertures to allow passage of wound fluid through the coated substrate. For example, an array of apertures may extend through said silicone coatings and the substrate layer. The open area of the coated substrate in the final product may for example be from about 1% to about 70%, for example from about 10% to about 50%.

The dressing materials of the invention are characterized by tacky upper and lower silicone coatings on the substrate, wherein the upper and lower silicone coatings have different tackiness. This provides the advantage that both surfaces can be protected before use by cover sheets adhered to the coating by the tackiness thereof, but one of the cover sheets can be removed more easily than the other whereby application of the dressing is easier. Not only is it easier to selectively remove the first cover sheet if it is less strongly adhered than the second cover sheet, but also the resulting exposed less-adherent surface is more suitable for application to the wound surface. The second cover sheet can then be removed to expose a more adherent surface for application of secondary dressing layers, such as absorbent layers.

The difference in tackiness between the upper and lower silicone coatings is suitably selected to optimise the above properties. For example, the tackiness of the lower surface as measured by a loop tack test (described below) is suitably from 5% to 150% greater than the tackiness of the upper surface, more suitably from 20% to 100% greater, for example about 30% to 70% greater. Suitably, the tackiness of the surfaces as measured by the loop tack test is greater than about 0.3N. For example, they may be from about 0.4N to about 2N, more suitably from about 0.5N to about 1.5N. In embodiments, the tackiness of one surface is from about 0.4N to about 1N and the tackness of the other surface is from about 0.5N to about 1.5N.

The present inventors have found ways in which the above difference in tackiness can be achieved in materials wherein the silicone on said upper and lower surfaces is substantially chemically homogeneous. That is to say, wherein the same silicone prepolymer is coated onto the upper and lower surfaces, but differences in curing conditions are used to achieve different tackiness in the upper and lower surfaces.

The total coating weight of the tacky silicone (combined upper and lower layers) is suitably from about 50 g/m$^2$ to about 500 g/m$^2$, for example from about 80 g/m$^2$ to about 200 g/m$^2$, typically from about 100 g/m$^2$ to about 150 g/m$^2$. The silicone is suitably a soft skin adhesive silicone composition. Suitably chemistry is described below. The silicone is suitably hydrophobic.

The effectiveness of encapsulation by silicone means that the substrate may be printed or dyed with decorative or informative matter with little danger of the ink or dye being released into the wound to which the dressing is applied. Visible indicia, such a colour or writing, may be provided on one or both of the surfaces of the substrate and/or on one or both cover sheets to indicate which sides of the product have the more/less tacky silicone coating and thus to indicate which cover sheet is removed first arid which silicone surface is less tacky for application to the wound surface.

The cover sheets may comprise a film of polyethylene, polypropylene or fluorocarbons and papers coated with these materials. Suitably, the cover sheet is a release-coated paper sheet, such as a silicone release-coated paper sheet Examples of silicone-coated release papers are POLYSLIK (Registered Trade Mark) supplied by H.P. Smith & Co., offered in various formulations to control the degree of adhesion of the paper to the adhesive surface.

In certain embodiments, one or both cover sheets may comprise two or more parts, such as a first removable part having a first edge and a second removable part that meets the first part along the first edge. Suitably, along each of said edges where the parts meet, one of the parts is folded back to provide a folded-back margin, and the other part overlaps the said folded-back margin. This provides an easy-to-grasp margin on each part in the region of overlap to assist removal of the cover sheet by the care giver.

In other embodiments, one or both cover sheets may comprise three parts, for example as described in detail in EP-A-0117632.

The products of the invention may be made into wound dressings for application to the surface of a wound by removing the top and bottom cover sheets. Suitably, the products of the invention consist essentially of the substrate, the silicone coatings, and the cover sheets. Suitably, the products of the invention are sterile and packaged in a microorganism-impermeable container.

In a further aspect, the invention provides a method of making a wound dressing material comprising:

providing a substrate layer having an upper surface and a lower surface;

coating said upper and lower surfaces of said substrate layer with a fluid silicone prepolymer composition; followed by thermally partially curing said silicone prepolymer composition to produce an intermediate material having a partially cured silicone composition on said upper and lower surfaces; followed by storing said intermediate material at a temperature below 50° C. for at least 2 days to allow equilibration of the silicone coatings on the upper and lower surfaces; followed by further curing said partially cured silicone composition by exposing said intermediate material to ionizing radiation, to produce a final material having tacky silicone coatings on said upper and lower surfaces.

In a further aspect, the invention provides a method of making a wound dressing material comprising:

providing a substrate layer having an upper surface and a lower surface;

coating said upper and lower surfaces of said substrate layer with a fluid silicone prepolymer composition; followed by thermally partially curing said silicone prepolymer composition to produce an intermediate material having a partially cured silicone composition on said upper and lower surfaces; followed by further curing said partially cured silicone composition by exposing said intermediate material to ionizing radiation, to produce a final material having tacky silicone coatings on said upper and lower surfaces, wherein either (a) said step of coating is applies unequal weights of the silicone coating composition to said upper and lower surfaces, and/or (b) said step of thermally partially curing applies different amounts of heat to said upper and lower surfaces, whereby said silicone coatings on said upper and lower surfaces have different tackiness following said further curing step.

The substrate layer is suitably as previously described for the products of the invention. Suitably, the substrate layer is permeable to the fluid silicone prepolymer composition. The step of coating may be performed in any conventional way, for example immersion, spraying, or doctor blade. The step of coating suitably comprises passing the coated substrate through nip rollers to ensure smooth coating and penetration of the coating composition. Suitably, the step of coating is followed by a step of blowing gas (such as air) through the substrate to ensure that the apertures in the material are open after coating.

The fluid silicone coating composition is suitably substantially or completely solvent-free. The methods of the present invention allow products having different tackiness on the upper and lower surfaces to be made with a single silicone coating composition on both surfaces.

Suitably, the silicone composition is a so-called soft skin adhesive silicone elastomer. Such silicones can be made by an addition reaction (hydrosilylation) between (a) a vinyl functional polydimethyl siloxane, such as bis-dimethyl vinyl PDMS, and (b) a hydrogen functional siloxane, such as dimethyl, methylhydrogen siloxane copolymers, hydrogen dimethylsiloxy terminated PDMS. The cure reaction is catalyzed by a hydrosilylation catalyst, such as a noble metal catalyst, suitably a platinum catalyst. Suitably the silicone prepolymer composition further comprises a polymerization inhibitor that is evaporated from said composition during said step of thermally partially curing, for example 2-methyl-3-butyn-2-ol. The polymerization inhibitor is suitably present in an amount of from about 0.001 wt. % to about 1 wt. %, for example from about 0.01 wt. % to about 0.1 wt. % before curing.

Silicone skin adhesive compositions are suitably supplied as two-part systems: Part A contains at least the vinyl prepolymer and the catalyst, while Part B contains the vinyl prepolymer and the SiH siloxane cross linker. The components are mixed immediately before use, optionally with addition of the polymerization inhibitor.

In embodiments, the silicone coating composition comprises or consists essentially of the following components:

(A) a diorganopolysiloxane having at least 2 alkenyl groups in each molecule;

(B) an organohydrogenpolysiloxane having at least 2 silicon-bonded hydrogen atoms in each molecule, in a quantity sufficient for the ratio between the number of moles of silicon-bonded hydrogen atoms in this component and the number of moles of alkenyl groups in component (A) to have a value of from about 0.6:1 to about 20:1, (C) optionally a platinum group metal catalyst suitably in a quantity providing 0.1 to 500 weight parts as platinum group metal per 1,000,000 weight parts component (A); and (D) a volatile polymerization inhibitor, suitably selected from: alkyne alcohols such as 2-methyl-3-butyn-2-ol, 3,5-dimethyl-1-hexyn-3-ol, and phenylbutynol; ene-yne compounds such as 3-methyl-3-penten-1-yne and 3,5-dimethyl-3-hexen-1-yne; tetramethyltetrahexenyl-cyclotetrasiloxane; and benzotriazole.

The diorganopolysiloxane, component (A), used in the instant invention is the base component of the total composition. This diorganopolysiloxane must contain at least 2 alkenyl groups in each molecule in order for this composition to cure into a rubbery elastic silicone rubber coating composition.

The diorganopolysiloxane (A) comprises essentially straight-chain organopolysiioxane with the average unit formula $R_nSiO(4-n)/2$, wherein R is selected from substituted and unsubstituted monovalent hydrocarbon groups and n has a value of 1.9 to 2.1. R may be exemplified by alkyl groups such as methyl, ethyl, propyl, and others; alkenyl groups such as vinyl, allyl, and others; aryl groups such as phenyl, and others; and haloalkyl groups such as 3,3,3-trifluoropropy 1 and others. The diorganopolysiloxane (A) should have a viscosity at 25° C. of at least 100 centipoise (1 d Pa·s). When such factors as the strength of the silicone rubber coating membrane, and blendability are taken into account, the viscosity of diorganopolysiloxane (A) at 25° C. is preferably from 1,000 centipoise (1 Pa·s) to 100,000 centipoise (100 Pa·s). The diorganopolysiloxane (A) may be exemplified by dimethylvinylsiloxy-endblocked dimethylpolysiloxanes, dimethylvinylsiloxy-endblocked dimethylsiloxane-methylvinylsiloxane copolymers, and dimethylvinyl-siloxy-endblocked dimethylsiloxane-methylphenylsiloxane copolymers.

Component (B), an organopolysiioxane that contains at least 2 silicon-bonded hydrogen atoms in each molecule, is a crosslinker for the composition of the instant invention. The organopolysiioxane (B) may be exemplified by trimethylsiloxy-endblocked methyi-hydrogenpolysiloxanes, trimethylsiloxy-endblocked dimethylsiloxanemethylhydrogen-siloxane copolymers, dimethylphenylsiloxy-endblocked methylphenylsiloxanemethyl-hydrogensiloxane copolymers, cyclic methyihydrogenpolysiloxanes, and copolymers that contain the dimethylhydrogensiloxy unit and $SiO4/2$ unit. The organohydrogenpolysiloxane (B) should be added in a quantity that the ratio between the number of moles of silicon-bonded hydrogen atoms in this organohydrogenpolysiloxane and the number of moles of alkenyl groups in component (A) has a value of 0.6:1 to 20:1.

The platinum group metal catalyst, component (C), used in the compositions is a curing catalyst. The platinum group metal catalyst (C) may be exemplified by platinum micropowder, platinum black, chloroplatinic acid, platinum tetrachloride, olefin complexes of chloroplatinic acid, alcohol solutions of chloroplatinic acid, complexes between chloroplatinic acid and alkenylsiloxanes, rhodium compounds, and palladium compounds. The platinum group metal catalyst (C) should be added generally at 0.1 to 500 weight parts as platinum group metal per 1,000,000 weight parts component (A), and is preferably used at 1 to 50 weight parts as platinum group metal per 1,000,000 weight parts component (A). The reaction will not develop adequately at less than 0.1 weight parts, while additions in excess of 500 weight parts are uneconomical.

The coated substrate is then subjected to thermal curing to partially cure the silicone. The thermal coating is suitably performed continuously by passing the coated substrate through an oven. Suitable thermal curing conditions include exposure to a temperature of from about 80° C. to about 200° C., for example about 120° C. to about 180° C. for a time of from about 1 minute to about 10 minutes, for example about 1.5 minutes to about 5 minutes. The elevated temperature results in evaporation of the polymerization inhibitor from the silicone composition and therefore in polymerization of the silicone. The resulting material is chemically polymerized, but capable of further curing by ionizing radiation as explained further below.

The partially cured material has unequal tackiness of the silicone coating on the upper and lower surfaces. This unequal tackiness can be produced by (1) unequal coating weights of the silicone on the upper and lower surface, and/or (2) the step of blowing air through the coated substrate to open the apertures, which results in a higher coating weight of silicone on the surface that is downstream of the air flow, and/or (3) unequal amounts of heat supplied to the upper and Lower surfaces in the oven resulting in different degrees of cure on the two surfaces.

The initial difference in tackiness of the upper and lower surfaces is typically rather greater than desired for the final product. However, the present inventors have found that the tackiness of the upper an lower surfaces gradually equilibrates if the partially cured material is stored at temperatures below about 50° C., for example ambient or near-ambient temperatures such as 10-50° C., for a period of from about 2 days to about 10 weeks. Therefore, suitably the partially cured material is stored at such temperatures for a period of at least about 2 days, suitably about 2 weeks to about 10 weeks, for example about 3 weeks to about 8 weeks before the final cure with ionizing radiation.

Suitably, the method of the invention further comprises applying upper and lower release sheets over said silicone composition on the upper and lower surfaces. Suitably, the upper and lower release sheets are applied intermediate said steps of thermally partially curing and storing, whereby, for example, the partially cured material having the cover sheets can be rolled up for the storage step.

The partially cured material is then subjected to a final cure with ionizing radiation. The ionizing radiation is suitably selected from e-beam radiation and gamma radiation. A variety of procedures for E-beam and gamma ray curing are well-known. The cure depends on the specific equipment used, and those skilled in the art can define a dose calibration model for the specific equipment, geometry, and line speed, as well as other well understood process parameters.

Commercially available electron beam generating equipment is readily available. For example, a Model CB-300 electron beam generating apparatus (available from Energy Sciences, Inc. (Wilmington, Mass.). Generally, a support film (e.g., polyester terephthalate support film) runs through a chamber. Generally, the chamber is flushed with an inert gas, e.g., nitrogen while the samples are e-beam cured. Multiple passes through the e-beam sterilizer may be needed.

Commercially available gamma irradiation equipment includes equipment often used for gamma irradiation sterilization of products for medical applications. Cobalt 60 sources are appropriate. Total absorbed doses are suitably from 20 to 60 kGy, more suitably from about 35 to 50 kGy and dose rates are suitably about 7 to 8 kGy/hour.

Suitably, the method further comprises the step of packaging the intermediate material in a microorganism-impermeable container prior to said step of further curing, and wherein said step of further curing also sterilizes the material.

The methods of the invention may be used to make any products according to the invention. Any feature disclosed herein in relation to any one or more aspects of the invention is suitable for use in any of the other aspects defined herein.

EXAMPLES

Specific embodiments of the invention will now be described further, by way of example, with reference to the accompanying drawings.

Referring to FIGS. 1 to 4, the product 1 according to the invention comprises a substrate 2 of cellulose acetate gauze of density 107 grams per square meter nominal, having upper and lower surfaces 4,5 coated with a hydrophobic, tacky, crosslinked silicone gel. The silicone composition penetrates the gauze substrate to form a single, chemically homogeneous silicone phase on the upper and lower surfaces. The coated substrate 6 has an array of apertures extending through the substrate and the silicone to allow passage of wound fluid through the material. The tackiness of the coated upper surface 4 is approximately 50% greater than the tackiness of the coated lower surface 5, as determined by the loop tack test described below. The nominal total coating weight of the silicone is 120-130 grams per square meter.

Figure 2:
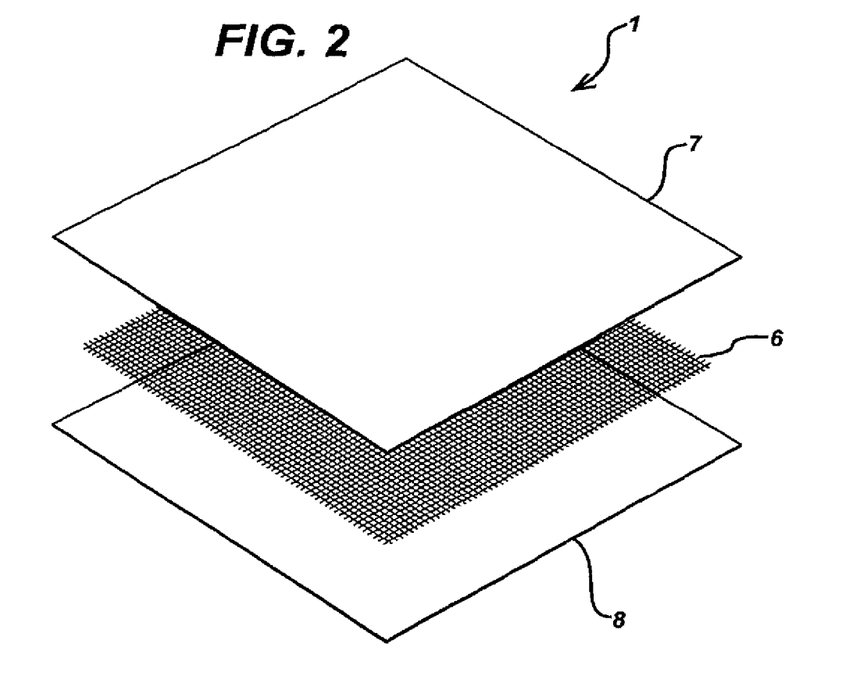
FIG. 2 shows a perspective exploded view of a product according to the invention.
Figure 3:
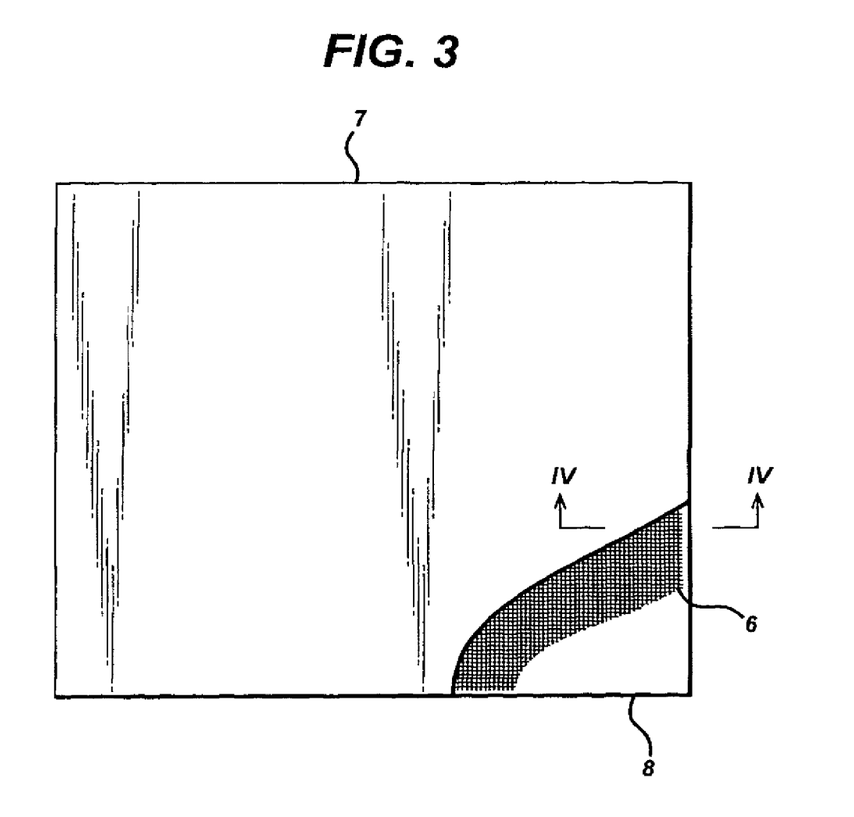
FIG. 3 shows a top plan view partially cut away of the product of FIG. 2.
Figure 4:
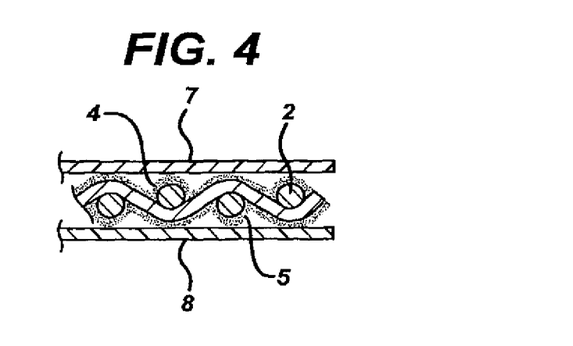
FIG. 4 shows an enlarged partial cross-section through the product of FIG. 2.

Identical release-coated cover sheets 7,8 are applied to the upper and lower silicone-coated surfaces 4,5. In use, the lower release sheet 8 is removed first to expose the less tacky lower surface 5 of the dressing material. It is relatively easy to selectively remove the lower release sheet 8 because of the lower adherency of this sheet to the material compared to the upper release sheet 1. The lower and/or upper release sheets may further comprise indicia to identify the release sheet to be removed first. The lower surface 5 may then be applied to a wound surface, followed by removal of the upper release sheet 7 and application of secondary dressing elements such as an absorbent layer.

Figure 1:
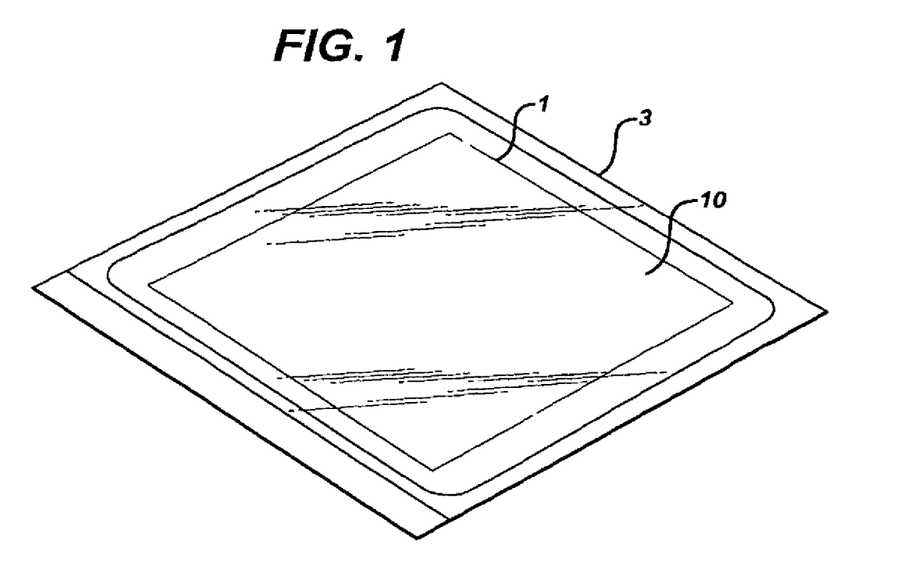
FIG. 1 shows a perspective view of a product according to the invention packaged in a microorganism-impermeable pouch.

Referring to FIG. 1, the product I is shown sterile and packaged in a microorganism-impermeable envelope 3 having a transparent window 10.

Figure 5:
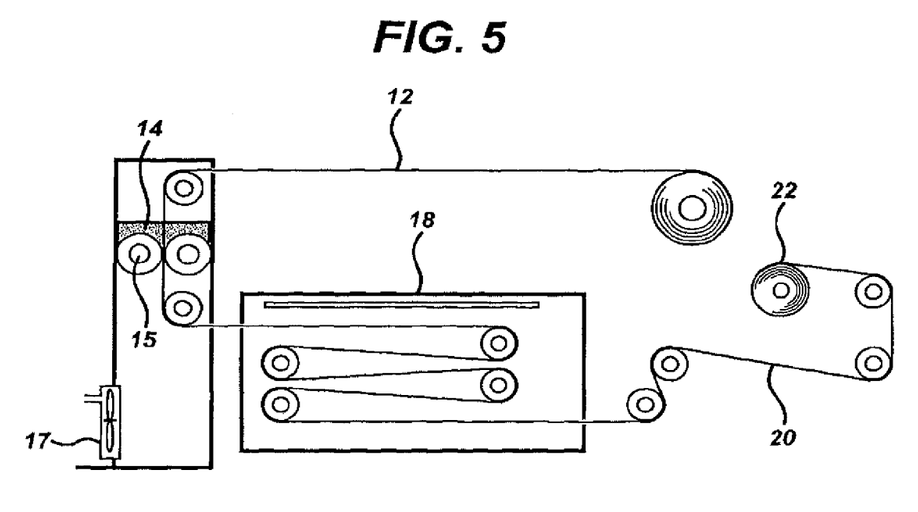
FIG. 5 shows a schematic view of an apparatus for making a product according to the method of the invention.

Referring to FIG. 5, the process according to the invention starts from a continuous web of cellulose acetate gauze 12 that is passed through a fluid silicone coating composition 14 and nip rollers 15 to coat and impregnate the gauze with the silicone composition. The silicone coating composition is prepared by mixing Components A and B of a soft silicone skin adhesive silicone elastomer kit supplied by Dow Corning under product reference Q7-9177. The components are mixed in weight ratio 50:50. Component A comprises a bis-dimethylvinyl terminated polydimethylsiloxane and a platinum catalyst. Component B comprises a bis-hydride terminated polydimethylsiloxane. To the mixture is added 2-methyl-3-butyn-2-ol inhibitor at a concentration of 0.02 wt. %.

The coated substrate then passes over a blower 17 to open the apertures of the coated substrate that may have been occluded by the silicone.

The coated gauze is then passed through an oven 18 held at 150° C. Typical conditions are 5 passes at 4.2 m/min, total residence time 1.5 minutes. This results in thermal partial cure of the silicone coating. The coated material is then allowed to cool, and release coated paper cover sheets (not shown) are then continuously applied to the upper and lower surfaces at location 20 and the material is rolled up on roll 22 for equilibration.

The rolls 22 of thermally cured and interleaved material are allowed to equilibrate at controlled temperature (20-25° C.) for 4-6 weeks. The material is then cut and packaged as shown in FIG. 1, followed by gamma irradiation with 35-50 kGy of Cobalt 60 radiation at 7-9 kGy/hr to sterilize the products and complete the cure. The irradiation curing results in a further increase in both hardness and tackiness of the silicone coating.

Procedure 1: Measurement of Surface Tackiness by the Loop Tack Test

Figure 6:
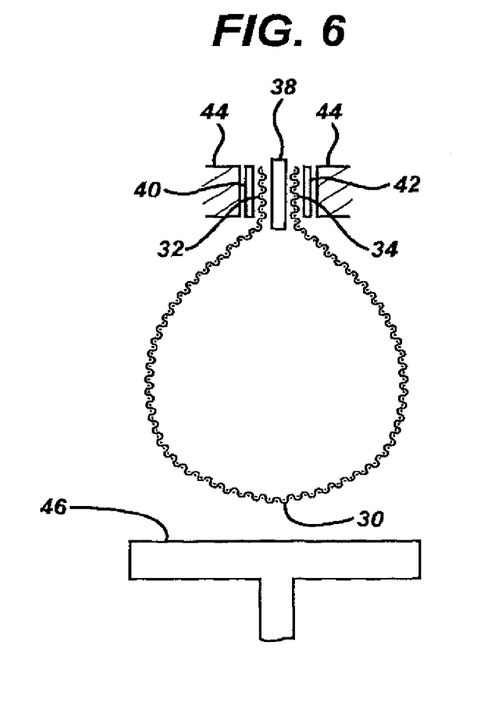
FIG. 6 shows a schematic diagram of the apparatus used for the loop tack measurement test.

The tackiness of the silicone coatings produced by the methods of the invention was measured in a tensile tester, such as an Instron tester, using the set-up shown in FIG. 6.

Samples of the coated fully cured gauze having the release cover sheets attached were cut to dimensions 5×9.5 cm. Margins of 1 cm were marked out along the long edges by drawing straight lines 1 cm from the long edges. The cover sheets were removed, and the sheet of coated gauze 30 was looped around and the 1 cm margins 32,34 on opposed edges of one surface (opposite the surface being measured) were applied firmly to opposite sides of a 2 mm thick metal spacer bar 38. Strips of polypropylene film 1 cm wide 40,42 were then applied to the opposite surfaces of the coated gauze opposite the spacer bar 38 to prevent the coated gauze from adhering to the jaws of the measurement device.

The assembly of polypropylene strips, coated gauze and spacer bar was then gripped in the jaws 44 of the Instron tester. The loop of coated gauze 30 having the surface under test outermost was then lowered onto a clean polycarbonate surface 46 of dimensions 15.5 cm×3.8 cm so that the loop adheres to the surface, and raised to detach the loop from the surface. Lowering and raising are performed at 300 mm/min, and the minimum distance between the jaws 44 and the polycarbonate surface 46 is 15 mm. The measured tack (in Newtons) is the maximum force measured while detaching the loop from the surface. Average of three measurements was used.

Figure 7:
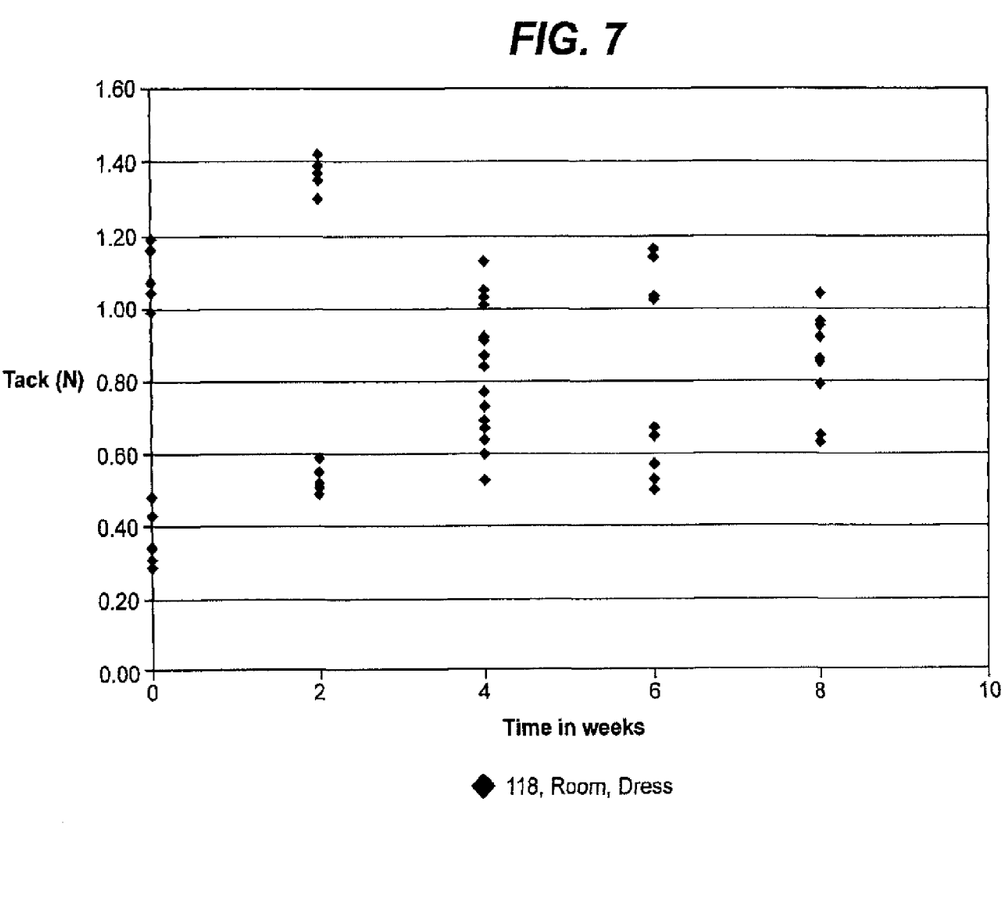
FIG. 7 shows a graph of measured loop tack adhesion for upper and lower surfaces of materials made in accordance with the present invention, wherein the samples have been stored for different times prior to the irradiation curing step.

FIG. 7 shows tack data obtained by the above for samples of the coated gauze obtained in accordance with the invention. The coating weight was 118 grams per square meter. Measurements were made on samples sterilized after storage at 25° C. and 4% relative humidity for 0, 2, 4, 6, and 8 weeks. The upper and lower surfaces initially have very different tack as evidenced by the two groups of measurements at around 0.4N and 1.1N, but the tack converges on storage after about 4 weeks such that the final tack of the upper surface is about 1.0N and the final tack of the lower surface is about 0.7N.

The above examples have been described by way of illustration only. Many other embodiments falling within the scope of the accompanying claims will be apparent to the skilled reader.

The invention claimed is:

1. A wound dressing product, comprising:
    a substrate layer having an upper surface and a lower surface; and
    a tacky silicone coating composition present on said upper surface and on said lower surface;
    wherein
        said tacky silicone coating composition is present in a greater weight on said upper surface than on said lower surface of said substrate layer;
        said upper surface is more tacky than said lower surface; and
        a tackiness of said upper surface as measured by a loop tack test is at from 20% to 100% greater than a tackiness of said lower surface.

2. The wound dressing product of claim 1, further comprising an upper release sheet adhered to said upper surface and a lower release sheet adhered to said lower surface.

3. The wound dressing product of claim 2, wherein said lower release sheet is adapted to be removed from said lower surface more readily than said upper release sheet can be removed from said upper surface.

4. The wound dressing product of claim 1, wherein said tacky silicone coating composition comprises a silicone prepolymer composition that has been cured thermally and by ionizing radiation.

5. The wound dressing product of claim 4, wherein said ionizing radiation is gamma radiation.

6. The wound dressing product of claim 1, wherein said tacky silicone coating composition is formed from a fluid silicone prepolymer composition comprising a vinyl functional polydimethylsiloxane, a hydrogen functional siloxane, a hydrosilylation catalyst, and a polymerization inhibitor.

7. The wound dressing product of claim 1, wherein said tacky silicone coating composition is hydrophobic, and does not include hydrophilic components.

8. The wound dressing product of claim 1, wherein an array of apertures extends through said silicone coatings and said substrate layer.

9. The wound dressing product of claim 1, wherein said silicone on said upper surface and said lower surface is substantially chemically homogeneous.

10. The wound dressing product of claim 1, wherein said substrate layer comprises a woven, nonwoven, or knitted mesh.

11. The wound dressing product of claim 1, which is sterile and packaged in a microorganism-impermeable container.

12. A wound dressing product comprising:
    a substrate layer having an upper surface and a lower surface;
    a tacky silicone coating composition present on said upper surface and on said lower surface; and
    upper and lower release sheets covering said substrate layer and said tacky silicone coating composition on said upper surface and said lower surface, respectively, and adhered to said surfaces by said tacky silicone coating composition, wherein the silicone coating composition on said upper surface is less tacky than the silicone coating composition on said lower surface whereby said upper release sheet can be removed from said upper surface more readily than said lower release sheet can be removed from said lower surface, wherein a tackiness of the lower surface as measured by a loop tack test is at from 20% to 100% greater than a tackiness of the upper surface.

13. The wound dressing product of claim 12, wherein an array of apertures extends through said silicone coating composition and said substrate layer.

14. The wound dressing product of claim 12, wherein said substrate layer comprises a woven, nonwoven or knitted mesh.

15. The wound dressing product of claim 12, wherein said silicone coating composition on said upper surface and said lower surface is chemically homogeneous.

16. The wound dressing product of claim 12, wherein said silicone coating composition on said upper surface and said lower surface has been formed by curing of a silicone prepolymer composition.

17. The wound dressing product of claim 12, which is sterile and packaged in a microorganism-impermeable container.

* * * * *